United States Patent [19]
Young et al.

[11] Patent Number: 5,368,025
[45] Date of Patent: Nov. 29, 1994

[54] NON-INVASIVE OXIMETER PROBE

[75] Inventors: Robert L. Young, Waukesha, Wis.;
Bert D. Heinzelman, Tenafly, N.J.;
David A. Lovejoy, Jupiter, Fla.

[73] Assignee: Sensor Devices, Inc., Waukesha, Wis.

[21] Appl. No.: 36,825

[22] Filed: Mar. 25, 1993

Related U.S. Application Data

[63] Continuation-in-part of Ser. No. 748,700, Aug. 22, 1991, Pat. No. 5,217,012.

[51] Int. Cl.⁵ ............................................. A61B 5/00
[52] U.S. Cl. ................................... 128/633; 128/666; 356/41
[58] Field of Search ........................... 128/633–634, 128/664–667; 356/39–41

[56] References Cited

U.S. PATENT DOCUMENTS

| | | |
|---|---|---|
| 3,599,629 | 8/1971 | Gordy . |
| 3,769,974 | 11/1973 | Smart et al. . |
| 4,091,803 | 5/1978 | Pinder . |
| 4,350,165 | 9/1982 | Striese . |
| 4,685,464 | 8/1987 | Goldberger et al. ............ 128/664 X |
| 4,830,014 | 5/1989 | Goodman et al. . |
| 4,865,038 | 9/1989 | Rich et al. ....................... 128/665 X |
| 4,867,165 | 9/1989 | Noller et al. . |
| 4,928,691 | 5/1990 | Nicolson et al. . |
| 4,974,591 | 12/1990 | Awazu et al. ................... 128/666 X |
| 5,035,243 | 7/1991 | Muz ................................. 128/633 |
| 5,054,488 | 10/1991 | Muz . |
| 5,058,588 | 10/1991 | Kaestle . |
| 5,209,230 | 5/1993 | Swedlow et al. ................ 128/665 X |

Primary Examiner—Angela D. Sykes
Attorney, Agent, or Firm—Foley & Lardner

[57] ABSTRACT

An improved noninvasive, electrooptical sensor probe is suitable for removable attachment to the skin of a patient to measure light extinction during transillumination of the blood-perfused tissue beneath the skin. According to the preferred embodiment of the probe, the probe has a unitary chassis having two widened ends connected by a flexible bridge. The topside of each widened end has a concave finger location saddle. The underside of the chassis has a cavity to receive an electrical sensor assembly including a light source and a photosensor. The probe further includes a foam backing having a front end connected to a back end by a neck, and two wings which extend laterally from opposing sides of the back end. The foam backing has an adhesive topside, which is bonded to the underside of the chassis to capture the electrical sensor assembly in the cavity of the chassis. Removable release tabs cover the adhesive topside of the wings prior to the application of the probe to a patient.

14 Claims, 4 Drawing Sheets

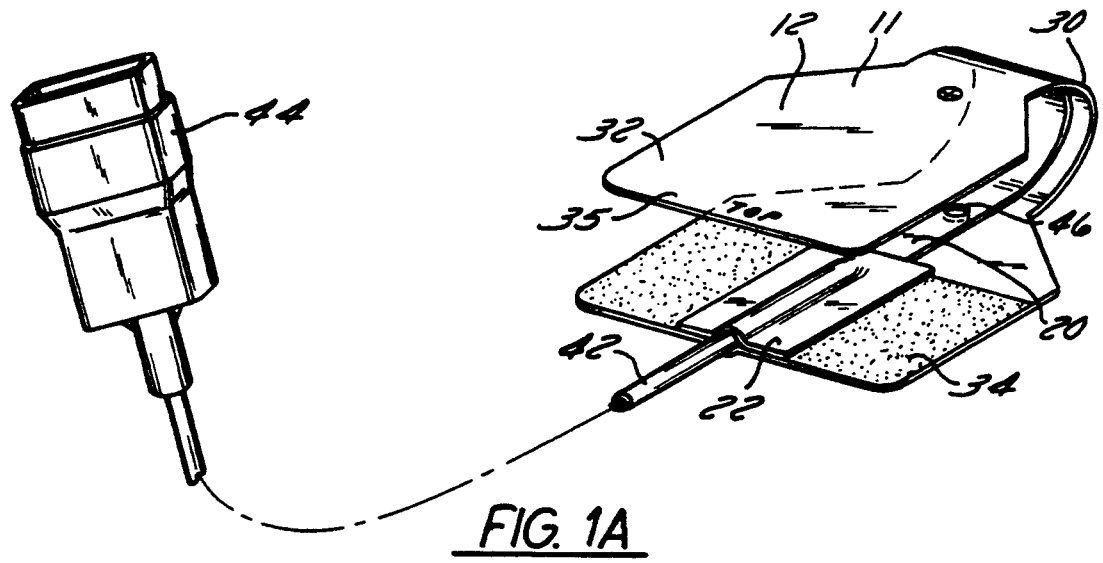
FIG. 1A
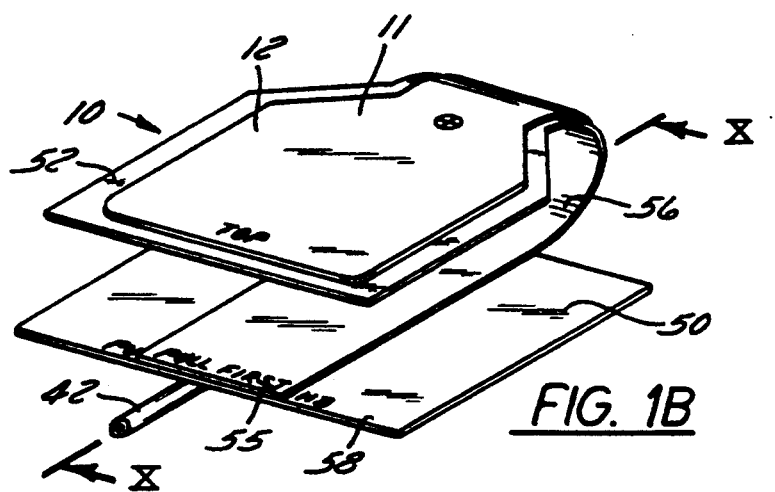
FIG. 1B
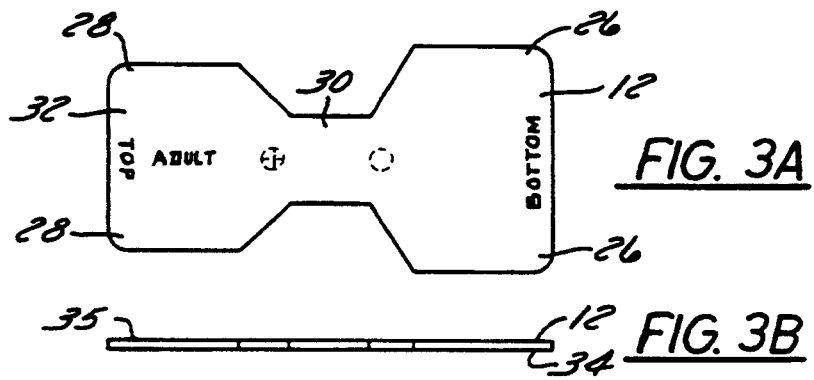
FIG. 3A
FIG. 3B

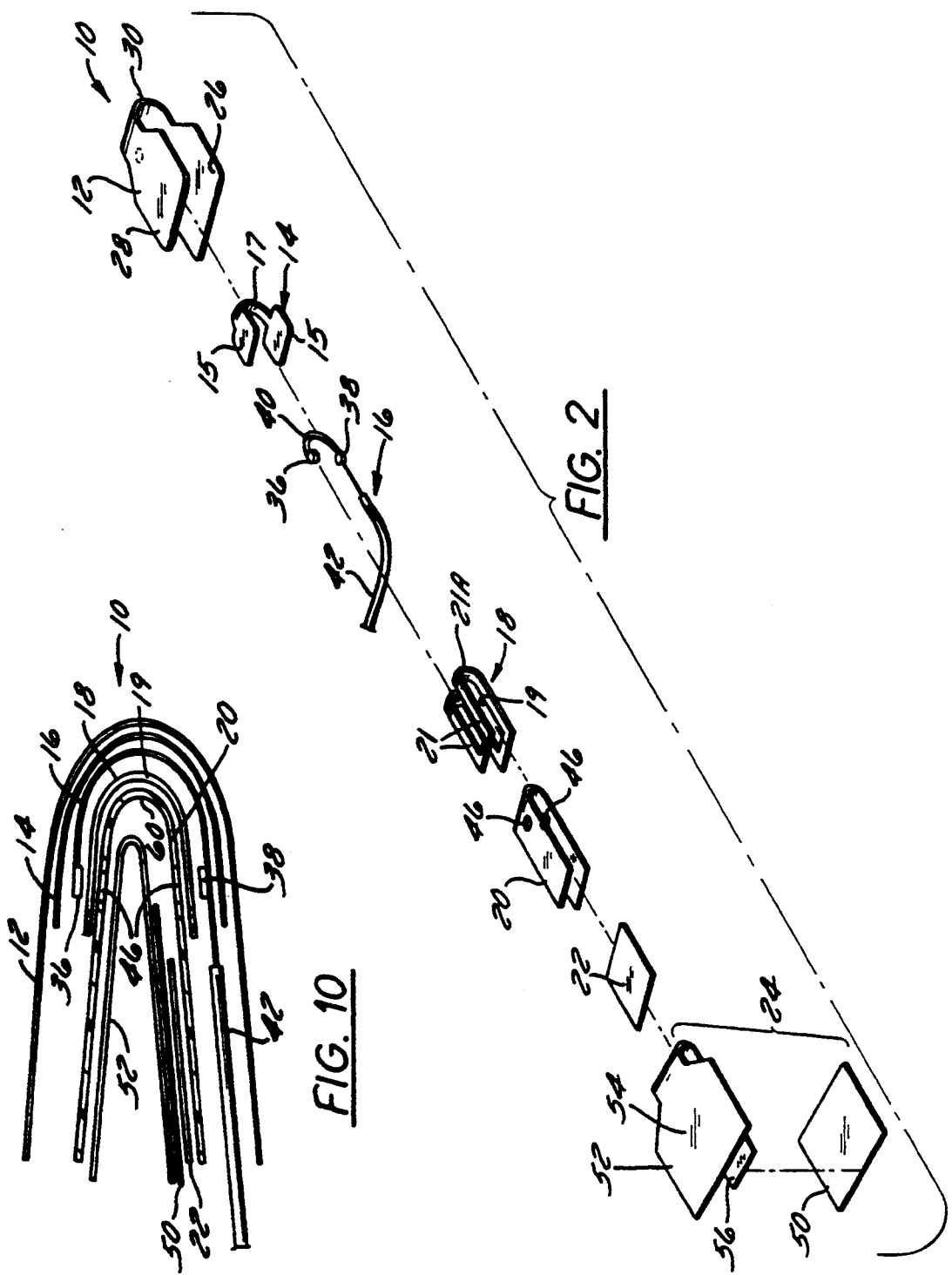

NON-INVASIVE OXIMETER PROBE

CROSS-REFERENCE TO RELATED APPLICATION

This application is a continuation-in-part of copending application Ser. No. 07/748,700 filed Aug. 22, 1991, now U.S. Pat. No. 5,217,012.

TECHNICAL FIELD

This invention relates generally to pulse oximetry, particularly to oximeter probes of the type which transmit light through blood-perfused tissue.

BACKGROUND OF THE INVENTION

Pulse oximetry involves the continuous, noninvasive monitoring of the oxygen saturation level in blood-perfused tissue to provide an early indication of impending shock. An oximeter probe (sensor) is secured to the patient and provides an electrical signal to an oximeter "box." The box houses electronic circuitry to process this electrical signal and generate human-readable indicia of the patient's blood oxygen saturation level.

Both disposable and non-disposable sensor probes for this purpose are widely used.

Current disposable probes typically comprise a flexible substrate (e.g., foam, fabric) having a light emitting diode (LED) and a photosensor spaced apart from one another and secured to the substrate. The substrate is adhesively attached to a patient's skin, preferably on the finger, nose, or ear of an adult, or on the foot of an infant. When the sensor is secured to the patient, the tissue is disposed between the LED and the photosensor such that light emitted by the LED passes through the tissue and is received by the photosensor.

Changes in the amount of light absorbed by the photosensor are caused by changes in the optical absorption of certain wavelengths by the blood-perfused tissue. The absorption characteristics of the transilluminated tissue are related to the oxygen saturation level of hemoglobin flowing through the tissue. These variations in light absorption caused by changes in oxygen saturation permit the direct, noninvasive monitoring of arterial oxygen content.

These and other similar medical devices are well known. See, for example, Smart et al. U.S. Pat. No. 3,769,974, which relates to a photo-optical blood pulse measurement transducer, and Pinder U.S. Pat. No. 4,091,803, which relates to a transducer for monitoring heart rate.

A variety of support structures have been devised for adhering probes and electrodes to skin surfaces. See, for example, Striese U.S. Pat. No. 4,350,165, and Gordy U.S. Pat. No. 3,599,629, which discloses a disposable biopotential skin electrode comprising a deformable, synthetic polymeric material having an adhesive coating.

Goodman et al. U.S. Pat. No. 4,830,014 describes a sensor for measuring arterial oxygen saturation using noninvasive photoelectric techniques. In a preferred embodiment, the sensor comprises a flexible, web-like, planar substrate having an LED mounted near a first end thereof and a photosensor spaced apart from the LED and mounted in a second end thereof. The sensor further includes an adhesive backing to facilitate close conformance to a patient's fingertip, such that the blood-perfused tissue lying between the LED and the photosensor is transilluminated by the light from the LED. Beginning at column 1, line 44, Goodman states that a common problem with existing oximeter sensors arises from their incompatibility with a patient's anatomy. More particularly, the physical construction of the sensors renders them bulky and difficult to securely fasten to a patient's appendage (e.g., finger, foot, nose, ear), resulting in differential motion between the patient and the sensor during patient movement. This relative motion, in turn, causes signal distortion (motion artifact.)

Prior art attempts to eliminate motion artifact often produced undesirable occluding effects due to, for example, the spring pressure applied by clip-like devices, resulting in insufficient pulse amplitude to reliably measure blood flow. Goodman attempts to solve this problem by integrating the light source and photosensor into the adhesive fastener.

While the integration of a light source and sensor into an adhesive structure serves to mitigate occlusion, it also tends to render the probe application procedure more difficult. For example, it is difficult to hold probes having an adhesive contact face during the application procedure without touching the exposed adhesive. It is also difficult to keep the opposing adhesive faces from adhering together prematurely. Further, the tie down procedure for such probes is not obvious to the user from the structure of the probes. Finally, once an adhesive probe's face has adhered to the finger of a patient, it is difficult to reposition the patient's finger when the probe light and sensor are misaligned.

The present invention improves upon the prior art probes by substantially changing the way in which the probe is mounted to an extremity and the way it maintains alignment between the LED and photosensor. In addition, the preferred embodiment of the present invention provides a probe which does not require direct adhesive contact with a patient's skin, which contact may traumatize the patient's cuticle tissue when attached to the patient's finger. The preferred embodiment of the present invention further provides centering and locating features to aid the user in positioning the patient's finger over the transducer pad.

SUMMARY OF THE INVENTION

According to one aspect of the present invention a noninvasive, electrooptical sensor probe for removable attachment to the skin of a patient to measure light extinction during transillumination of the blood-perfused tissue beneath the skin includes a chassis having a topside and an underside and having a first end connected to a second end by a flexible bridge. The topside of the first and second ends are spaced and opposed when the bridge is folded in a U-shape, and the topside of at least one of the first or second ends forms a concave finger location saddle. The probe further includes a light source mounted on the first end of the chassis and a photosensor mounted on the second end of the chassis positioned to detect light emitted by the light source when the bridge is folded in a U-shape. The finger location saddle conforms to the curvature of the patient's finger and serves both to properly position the light source and photosensor relative to the finger and to create a snug interface between the probe and the tissue of the finger to better isolate the tissue from extraneous light sources. The probe also includes means for electrically connecting the light source and the photosensor to an external device and means for removably securing the chassis to the skin.

According to another aspect of the present invention, a noninvasive, electrooptical sensor probe for removable attachment to the skin of a patient to measure light extinction during transillumination of the blood-perfused tissue beneath the skin includes a unitary, molded chassis having a topside and an underside and having a first end connected to a second end by a flexible bridge. The topside of the first and second ends are spaced and opposed when the bridge is folded in a U-shape. A light source is mounted on the first end of the chassis and a photosensor is mounted on the second end of the chassis positioned to detect light emitted by the light source when the bridge is folded in a U-shape. The probe further includes means for electrically connecting the light source and the photosensor to an external device and means for removably securing the chassis to the skin.

According to yet another aspect of the invention, a noninvasive, electrooptical sensor probe for removable attachment to the skin of a patient to measure light extinction during transillumination of the blood-perfused tissue beneath the skin, includes a chassis having a nonadhesive topside and an underside, and having a first end connected to a second end by a flexible bridge. The topside of the first and second ends are spaced and opposed when the bridge is folded in a U-shape. The probe further includes an electrical sensor assembly including a light source and a photosensor. The sensor assembly is mounted on the chassis whereby the light source is at the first end of the chassis and the photosensor is at the second end of the chassis. The photosensor is positioned to detect light emitted by the light source when the bridge is folded in a U-shape. The probe further includes means for electrically connecting the light source and the photosensor to an external device and means for removably securing the chassis to the skin.

According to another aspect of the present invention, a noninvasive, electrooptical sensor probe for removable attachment to the skin of a patient to measure light extinction during transillumination of the blood-perfused tissue beneath the skin includes a unitary, molded chassis having a nonadhesive topside and an underside, and having a first end connected to a second end by a flexible bridge. The topside of the first and second ends are spaced and opposed when the bridge is folded in a U-shape. The topside of the chassis includes a finger location saddle on at least one of the first or second ends, a light source mounted on the first end of the chassis, and a photosensor mounted on the second end of the chassis. The photosensor is positioned to detect light emitted by the light source when the bridge is folded in a U-shape. The probe further includes means for electrically connecting the light source and the photosensor to an external device, and means for removably securing the chassis to the skin.

BRIEF DESCRIPTION OF THE DRAWINGS

The probe of the invention is described below in conjunction with the appended drawings, wherein like designations denote like elements, and:

FIG. 1A is a perspective view of a sensor probe according to the invention for adult use with release tapes removed to show a slide which facilitates insertion of the patient's finger into the probe;

FIG. 1B is the same view as FIG. 1A, showing release tapes adhered to the inner surface of the probe;

FIG. 2 is an exploded view of the probe shown in FIG. 1B;

FIGS. 3A and 3B are plan and side views, respectively, of the outer tape shown in FIGS. 1A, 1B and 2;

FIG. 10 is an exploded, cross-sectional view taken along line X—X in FIG. 1B;

DETAILED DESCRIPTION OF PREFERRED EMBODIMENTS

Figure 4:
FIG. 4 is a plan view of the light block tape shown in FIG. 2.

With reference to FIGS. 1A, 1B, 2 and 10, a generally U-shaped probe 10 according to the invention includes a web-like support structure 11 (including an outer tape 12, a light block tape 14, and other components as described below), an electrical sensor assembly 16, an alignment member 18, an inner tape 20, a positioning slide 22, and a release tape assembly 24. During manufacture, the foregoing components are sequentially assembled, such as shown in FIG. 2, into the U-shaped sensor shown in FIG. 1B.

Referring to FIGS. 3A and 3B, outer tape 12 has a pair of laterally extending, generally rectangular bottom wings 26 at one end thereof, a similar, slightly shorter pair of lateral top wings 28 at the other end thereof, and a narrow bridging portion (bight) 30 therebetween. The words "Top", "Bottom", and "Adult" and other suitable symbols may be printed on an outer surface 32 of tape 12 to aid in the identification of the probe and to facilitate application to a patient. Tape 12 has an inner surface including a lower inner surface 34 and an upper inner surface 35 which are spaced from each other. Inner surfaces 34, 35 of outer tape 12 are coated with a pressure sensitive adhesive at wings 26, 28 for securing probe 10 to the skin. Outer tape 12 is preferably made from an opaque microfoam material, for example, Stock No. 977L, manufactured by the 3M Company of St. Paul, Minn.

Referring to FIGS. 2 and 4, light block tape 14, preferably adhesive-coated on both sides, may be made from a material known in the industry as Kodak Optical Flat Black. In the illustrated embodiment, light block 14 comprises a pair of flat, preferably square end portions 15 spanned by a narrow central connecting portion 17. In an alternative embodiment, portion 17 is omitted, and opposed, flat plates 15 comprise separate pieces. At least one side of light block tape 14 bears a black light block layer (e.g., Coating Sciences #S121). Light block tape 14, of smaller dimensions than outer tape 12, overlies a portion of lower inner surface 34 of outer tape 12 and isolates the transilluminated tissue from extraneous light sources (e.g., room lighting, sunlight, etc.), thereby improving the signal-to-noise ratio of probe 10.

Figure 5:
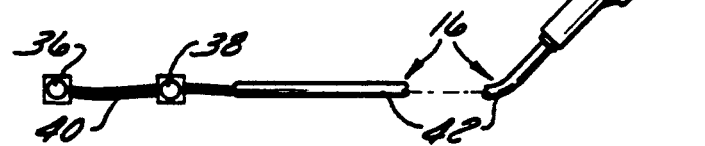
FIG. 5 is a plan view of the sensor assembly shown in FIG. 2.

Sensor assembly 16, shown in FIG. 5, includes a miniature light-emitting diode (LED) 36, a miniature photoreceptor (photosensor) 38, and lead wires 40 connecting the LED 36 and photosensor 38 to a cable 42. A 9-pin plug connector 44, attached to the other end of the cable 42, is configured to interface with a conventional oximeter box (not shown). Sensor assembly 16 is adhesively secured to light block tape 14 with LED 36 and photosensor 38 disposed at the center of each of square end portions 15 (see FIG. 10) and wires 40 extending along connecting portion 17.

Figure 7:
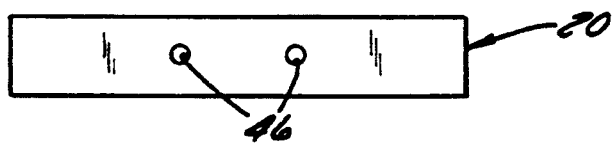
FIG. 7 is a plan view of the inner tape shown in FIG. 2.

Inner tape 20, preferably adhesive coated on both sides, secures assembly 16 and alignment member 18 to outer tape 12. Inner tape 20 includes respective spaced windows 46 of transparent plastic (FIG. 7) positioned over and in registration with each of LED 36 and photosensor 38. Inner tape 20 is preferably opaque other than at windows 46, and may comprise one tape as shown or three pieces of tape overlying one another, e.g., one at each ends and a central tape having windows 46 overlying the ends of the other two.

U-shaped alignment member 18 is disposed between light block tape 14 and inner tape 20 to maintain the overall configuration of the device, and particularly to maintain alignment between the LED and photosensor. In the illustrated embodiment, member 18 is a thin, resilient, flat, elongated (generally rectangular) piece of plastic having a central slot or gap 19 which extends more than half the length of member 18. LED 36 and photosensor 38 are positioned within slot 19 near opposite ends thereof. Parallel rod portions 21 of member 18 on either side of slot 19 preform probe 10 into a U-shaped configuration which renders probe 10 easier to mount on a human extremity, particularly a finger. Rods 21 each have curved, preferably semicircular bight portions 21A (FIG. 6A) so that straight, upper and lower leg portions 21B thereof are generally parallel to each other (see FIG. 6A). In an alternative embodiment shown in FIG. 6B, an alignment member 18A is fashioned in a bent U-shape with only one curved end connecting portion 23, rather than two end portions as shown in FIG. 2.

Alignment member 18 or 18A is preferably made from a lightweight, shape-retentive polypropylene such as FINA 3622 manufactured by the Fina Oil and Chemical Company of Dallas, Tex. Alignment member 18 or 18A is preferably highly resilient, i.e., sufficiently resilient so that alignment member 18 can assume a substantially planar configuration without breaking during assembly of probe 10. When the fully assembled probe 10 is removed from the assembly tooling, alignment member 18 or 18A instantly snaps back to its overall U-shaped configuration. By means of the shape memory of member 18 or 18A, probe 10 assumes a corresponding U-shaped configuration when undeformed, as shown in FIG. 1B.

Conventional flexible, planar sensors suffer the inherent problem of requiring precise manual alignment of the LED opposite the photosensor so that the maximum amount of light emitted by the LED is received by the photosensor. Inasmuch as the undersurface of existing sensors is typically coated with a pressure sensitive adhesive, the sensor has a tendency to adhere to the patient before a physician or technician can establish the optimum alignment between the LED and photosensor. Moreover, it is cumbersome to remove the sensor and re-apply it to the patient to compensate for misalignment between the LED and photosensor. The problem is exacerbated in many critical care applications, for example, during emergency surgery, when health care professionals often lack the time to ensure proper alignment between the LED and photosensor. As a result, sometimes only a small fraction of the light emitted by the LED is received by the photosensor.

Figure 8:
FIG. 8 is a plan view of the positioning slide shown in FIG. 2.
Figure 9:
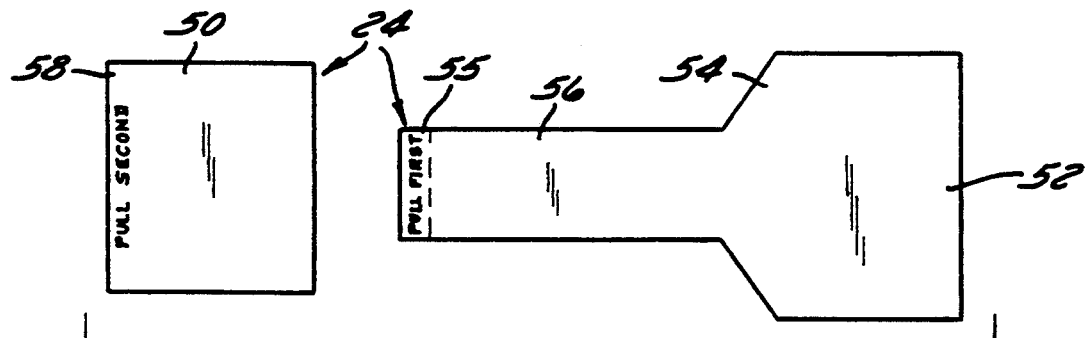
FIG. 9 is a plan view of the release tape assembly shown in FIGS. 1B and 2.

In the probe of the invention these problems are addressed not only by the overall U-shaped configuration of probe 10 provided by alignment member 18, but also by the provision of positioning slide 22 which further facilitates proper alignment of the LED and photosensor. As shown in FIGS. 1A, 2 and 8, positioning slide 22 comprises a rectangular piece of a smooth-surfaced plastic tape free of adhesive on its outer surface. Slide 22 is disposed on adhesive-coated lower inner surface 34 of outer tape 12 covering cable 42. In this way, the inner rectangular region of lower surface 34 defined by the positioning slide 22 remains adhesive-free, thus permitting the patient's finger to move freely along the positioning slide 22 until the finger abuts the bottom U-shaped end of probe 10. This reduces the risk that the sensor will stick to the patient before the LED 36 and photosensor 38 can be properly aligned.

Referring now to FIGS. 1B, 2, 9, and 10, release tape assembly 24 includes release tapes 50 and 52 configured to releasably adhere to the inside surface of probe 10. More particularly, release tape 50 overlies bottom wings 26 of outer tape 12, concealing positioning slide 22 and portions of inner tape 20, electrical assembly 16, alignment member 18, and light block 14. Tape 52 comprises an enlarged end portion 54 and a pull tab 56. End portion 54 overlies top wings 28 of outer tape 12 and conceals the remaining portion of the inside surface of the probe. Pull tab 56 extends freely over release tape 50. Release tape assembly 24 thus protects the adhesive surfaces of probe 10 until it is ready for use.

To apply probe 10 to a patient, the user first pulls upon the end 55 of pull tab 56 to remove release tape 52 and fully expose release tape 50. Release tape 50 is then removed by pulling up its outer edge 58, exposing lower inner surface 34 of outer tape 12 and the various subcomponents, all of which are adhesive-coated except for the central, adhesive-free area defined by positioning slide 22 on lower inner surface 34. The patient's finger is then guided along positioning slide 22, passing through an imaginary line between LED 36 and photosensor 38, until the finger abuts the closed, U-shaped, inner end 60 of probe 10. When probe 10 is applied to a patient in the foregoing manner, alignment member 18 ensures proper alignment of the patient's finger, LED 36, and photosensor 38 without the need for the user to manually align the LED and photosensor.

Certain features of probe 10 according to the invention, particularly size and precise configuration, are dictated by the intended end use. Oximeter probes according to the present invention are preferably made in sizes for adult, pediatric, infant and neonatal use.

Figure 11:
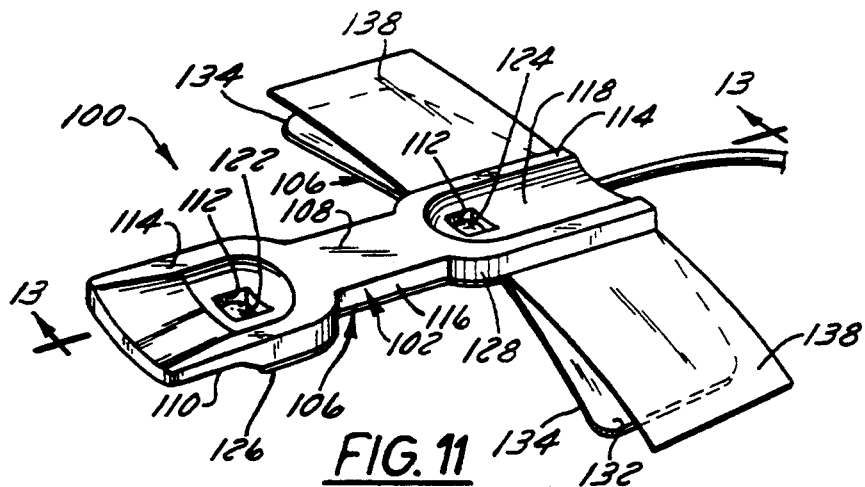
FIG. 11 is a perspective view of a probe according to the preferred embodiment of the present invention.
Figure 12:
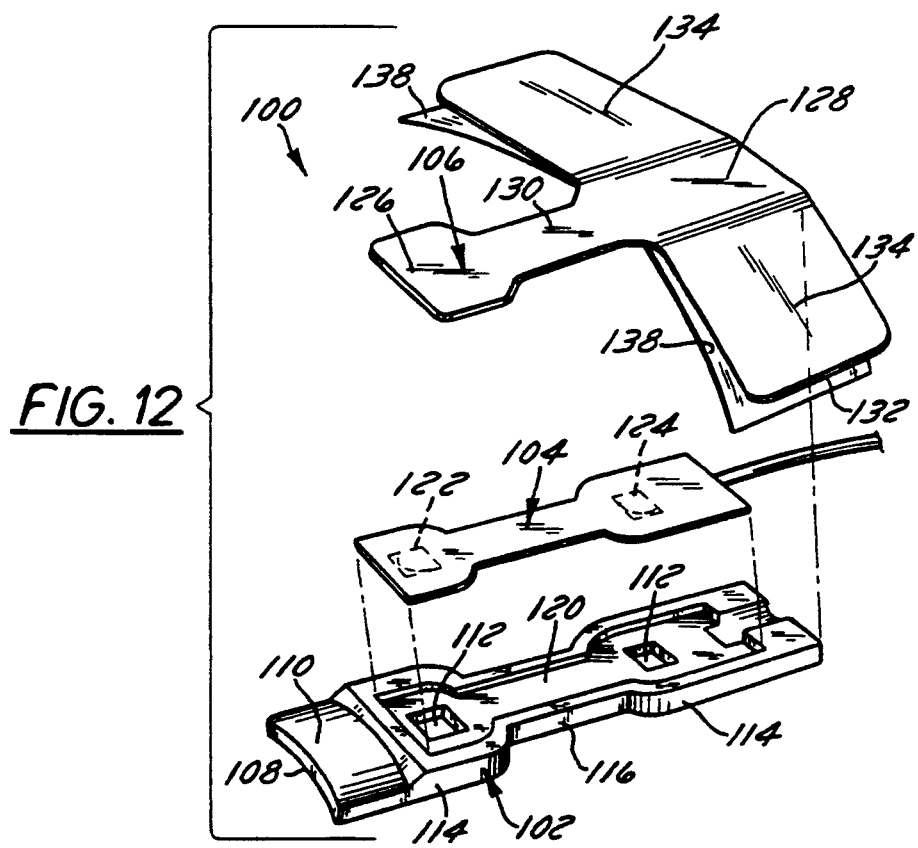
FIG. 12 is an exploded, perspective view of the probe shown in FIG. 11.
Figure 13:
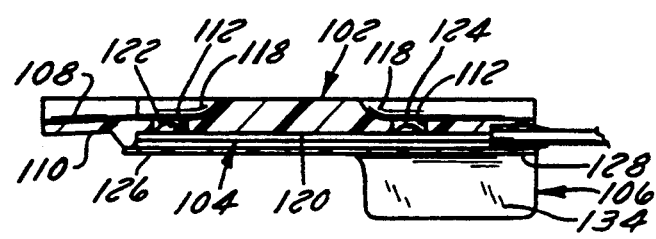
FIG. 13 is a longitudinal sectional view of the probe shown in FIG. 11 taken along line 13—13.

Referring to FIGS. 11-13, an oximeter probe 100 is shown according to an alternative, preferred embodiment of the present invention. Probe 100 generally comprises a molded, flexible chassis 102, an electrical sensor assembly 104, and a winged backing 106. The chassis 102 is preferably a unitary component formed by injection molding, and has first and second widened ends 114 connected by a flexible bridge 116. The chassis 102 has two windows 112, one in each of the widened ends 114.

Chassis 102 has a nonadhesive, opaque topside 108 and an underside 110. The topside 108 of the widened ends 114 of the chassis 102 define finger location saddles 118. The finger location saddles 118 are concave and extend from the outer edge of the widened ends 114 to the bridge 116. The windows 112 are within the finger location saddles 118. Thus, bridge 116 is may be folded in a U-shape to cause the windows 112 and the finger location saddles 118 to face each other.

The underside 110 of the chassis 102 has a cavity 120 for receiving the flexible sensor assembly 104. During assembly, chassis 102 is held topside 108 down allowing the underside 110 of the chassis 102 to act as a fixture for the assembly of the sensor assembly 104.

The sensor assembly 104 may be secured in the cavity 120 by tape (not shown) or, preferably, the sensor assembly 104 may be molded into the chassis 102 itself.

The flexible sensor assembly 104 contains an LED 122 and a photosensor 124. LED 122 and photosensor 124 are spaced to align with windows 112 when the electrical sensor assembly 104 is inserted into cavity 120 on chassis 102.

Backing 106 is preferably made of die-cut foam and has a front end 126 connected to a back end 128 by a neck 130. Two opposing wings 134 extend laterally from the back end 128 of the backing 106. The backing 106 has an adhesive topside 132 which, on the wings 134, is covered by release tabs 138. The adhesive topside 132 of the backing 106 is disposed to adhere to the underside 110 of the chassis 102 over cavity 120 to capture the electrical sensor assembly 104 between the backing 106 and the chassis 102.

To apply the probe 100 to a patient, the user first places one side of a finger of the patient in one of the finger location saddles 118. Next, the flexible bridge 116 is bent in a U-shape around the extremity of the finger to locate the other side of the patient's finger in the other one of the finger location saddles 118. The finger location saddles 118 conform to the curvature of the patient's finger and serve both to properly position the finger relative to electrical sensor assembly 104 within the probe 100, and to create a snug interface between the probe 100 and the tissue of the finger to better isolate the tissue from extraneous light sources. Next, one of the release tabs 138 is removed to expose the adhesive top side of a first one of the wings 134. The first one of the wings 134 is then folded around the side of the patient's finger and adhesively bonded to bottom side of the front end 126 of the backing 106. The other of the release tabs 138 is then removed to expose the adhesive top side of the second of the wings 134. Finally, the second of the wings 134 is similarly folded around the other side of the patient's finger and adhesively bonded to the backside of the first wing. Because the release tabs 138 need not be removed from the wings 134 until the patient's finger is already properly positioned in the probe 100, the possibility of inadvertent bonding to the patient, to the probe 100 itself, or to any other contact surface is significantly reduced. In addition, with the proper selection of adhesive characteristics, probe 100 may be removed and repositioned on a patient's finger since the adhesive never touches the skin of the patient.

Figures 6A, 6B:
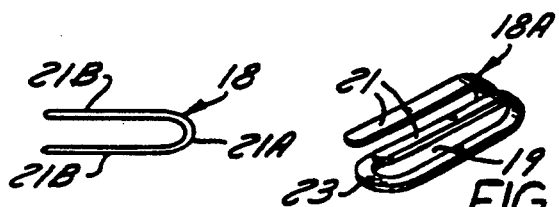
FIG. 6A is a side view of the alignment member shown in FIG. 2.
FIG. 6B is a perspective view of an alternative embodiment of an alignment member of the invention.

In an alternative embodiment, probe 100 may further comprise a resilient U-shaped alignment member similar to the alignment member 18 shown in FIGS. 2, 6A and 6B. The curved portion of the alignment member would be disposed adjacent to the flexible bridge 116 to impart a U-shape thereto, thus alleviating the need for the step of bending the flexible bridge 116 around the finger of the patient in the application procedure. The alignment member would further ensure that proper alignment is maintained between the LED 122 and photosensor 124. It will be understood that the foregoing description is of preferred exemplary embodiments of the invention, and that the invention is not limited to the specific forms shown. For example, a variety of thin, flexible materials could be substituted for the particular tapes and plastics described, and means other than adhesives, such as hook-and-loop closures or other fasteners, could be used to secure the probe to the patient. These and other modifications may be made in the design and arrangement of the elements without departing from the scope of the invention as expressed in the appended claims.

What is claimed is:

1. A noninvasive, electrooptical sensor probe for removable attachment to the skin of a patient to measure light extinction during transillumination of the blood-perfused tissue beneath the skin, comprising:

a unitary elastomeric polymeric chassis having a topside and an underside and having a first end connected to a second end by a flexible bridge, whereby the topside of said first and second ends are spaced and opposed when the bridge is folded in a U-shape, and wherein the topside of at least one of said first or second ends forms a concave finger location saddle;

a light source mounted on the first end of said chassis;

a photosensor mounted on the second end of said chassis positioned to detect light emitted by said light source when the bridge is folded in a U-shape;

means for electrically connecting said light source and said photosensor to an external device; and means for removably securing said chassis to the skin, wherein said means for removably securing said chassis comprises first and second wings extending from opposing lateral sides of one of first or second ends of said chassis.

2. The sensor probe of claim 1 wherein the underside of said chassis includes a cavity, wherein said light source and said photosensor are disposed within said cavity, and wherein said sensor probe further includes means for covering said cavity to capture said light source and said photosensor therein.

3. The sensor probe of claim 1 wherein the topside of the other of said first or second ends forms a second finger location saddle.

4. The sensor probe of claim 1 further comprising a highly resilient, generally U-shaped alignment member for imparting a U-shape to the bridge of said chassis.

5. The sensor probe of claim 1 wherein each of said first and second wings has at least one adhesive side, and wherein the adhesive sides of said first and second wings are covered by first and second release tabs, respectively, prior to the attachment of the sensor probe to the patient.

6. The sensor probe of claim 1 wherein the topside of said chassis is opaque to visible light.

7. A noninvasive, electrooptical sensor probe for removable attachment to the skin of a patient to measure light extinction during transillumination of the blood-perfused tissue beneath the skin, comprising:

a unitary, molded chassis having a topside and an underside and having a first end connected to a second end by a flexible bridge, whereby the topside of said first and second ends are spaced and opposed when the bridge is folded in a U-shape;

a light source mounted on the first end of said chassis;

a photosensor mounted on the second end of said chassis positioned to detect light emitted by said light source when the bridge is folded in a U-shape;

means for electrically connecting said light source and said photosensor to an external device;

and means for removably securing said chassis to the skin, wherein said means for removably securing said chassis comprises first and seconded wings having at least one adhesive side, wherein said first and second wings extend from opposing lateral sides of one of said first or second ends of said chassis.

8. The sensor probe of claim 7 wherein the underside of said chassis includes a cavity, wherein said light source and said photosensor are disposed within said cavity, and wherein said sensor probe further includes means for covering said cavity to capture said light source and said photosensor therein.

9. The sensor probe of claim 7 wherein the topside of one of said first or second ends forms a finger location saddle.

10. The sensor probe of claim 7 further comprising a highly resilient, generally U-shaped alignment member for imparting a U-shape to the bridge of said chassis.

11. The sensor probe of claim 7 wherein the topside of said chassis is opaque to visible light.

12. A noninvasive, electrooptical sensor probe for removable attachment to the skin of a patient to measure light extinction during transillumination of the blood-perfused tissue beneath the skin, comprising:

a unitary, molded elastomeric polymeric chassis having a nonadhesive topside and an underside, and having a first end connected to a second end by a flexible bridge, whereby the topside of said first and second ends are spaced and opposed when the bridge is folded in a U-shape;

an electrical sensor assembly including a light source and a photosensor, said sensor assembly being mounted on said chassis whereby said light source is at said first end of said chassis and said photosensor is at said second end of said chassis, and wherein said photosensor is positioned to detect light emitted by said light source when the bridge is folded in a U-shape;

means for electrically connecting said light source and said photosensor to an external device; and means for removably securing said chassis to the skin, wherein the means for removably securing said chassis to the skin comprises a first and second flexible wing, wherein said first wing extends Laterally from one side of one of said first and second ends of said chassis, wherein said second wing extends laterally from the other side of said one of said first and second ends of said chassis, wherein said wings have a topside and an underside, wherein the topside side of said wings faces the same direction as the topside of the chassis, and wherein said underside of said wings is adhesive.

13. The sensor probe of claim 12 wherein the topsides of said first and second ends form finger location saddles.

14. A noninvasive, electrooptical sensor probe for removable attachment to the skin of a patient to measure light extinction during transillumination of the blood-perfused tissue beneath the skin, comprising:

a unitary, molded elastomeric polymeric chassis having a nonadhesive topside and an underside, and having a first end connected to a second end by a flexible bridge, whereby the topside of said first and second ends are spaced and opposed when the bridge is folded in a U-shape, and wherein the topside of said chassis includes a finger location saddle on at least one of said first or second ends;

a light source mounted on the first end of said chassis;

a photosensor mounted on the second end of said chassis positioned to detect light emitted by said light source when the bridge is folded in a U-shape;

means for electrically connecting said light source and said photosensor to an external device; and means for removably securing said chassis to the skin, wherein said means for removably securing said chassis comprises first and second wings extending from opposing lateral sides of one of said first or second ends of said chassis.

* * * * *